Figure 1:
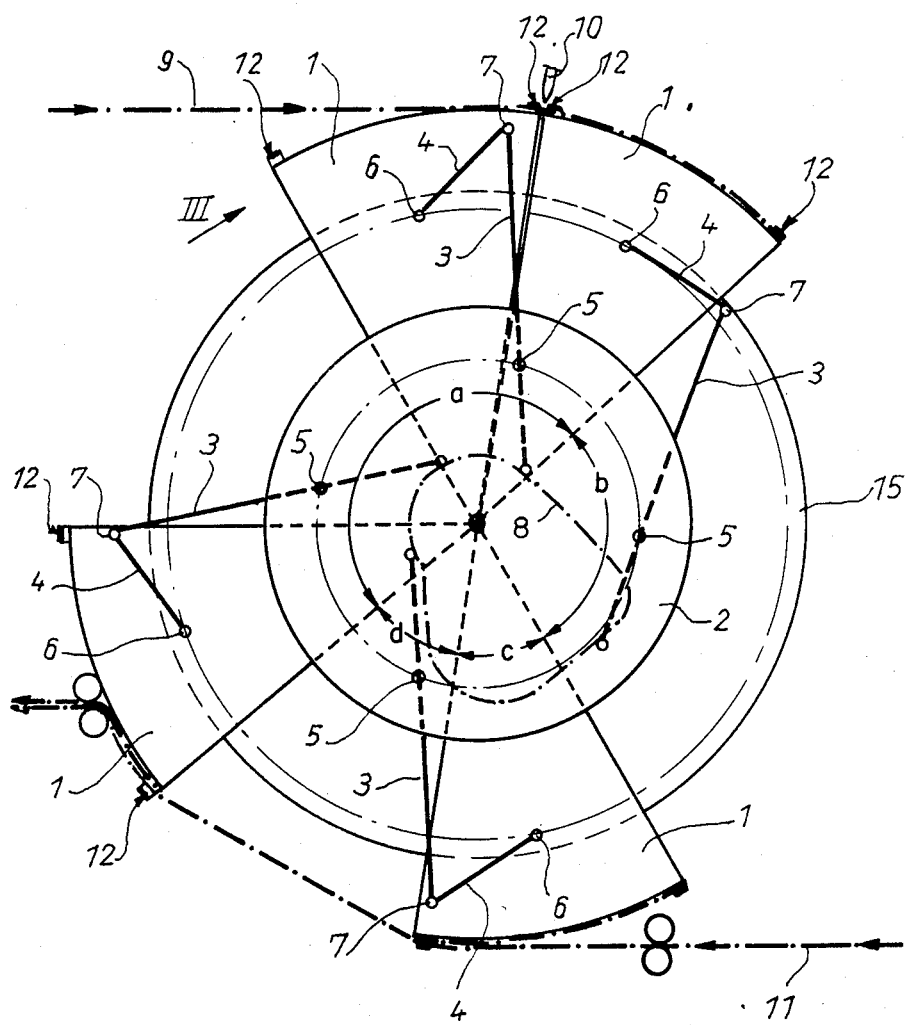

United States Patent [19]

Eschler

[11] Patent Number: 4,610,751
[45] Date of Patent: Sep. 9, 1986

[54] APPARATUS FOR SEPARATING AND APPLYING OF SECTIONS OF STRIPS ON AREAS OF A MATERIAL WEB LYING AT A DISTANCE ONE BEHIND THE OTHER

[75] Inventor: Dieter Eschler, Heidenheim, Fed. Rep. of Germany

[73] Assignee: Paul Hartmann Aktiengesellschaft, Heidenheim, Fed. Rep. of Germany

[21] Appl. No.: 663,374

[22] Filed: Oct. 22, 1984

[30] Foreign Application Priority Data

Oct. 21, 1983 [DE] Fed. Rep. of Germany ....... 3338306
Aug. 30, 1984 [DE] Fed. Rep. of Germany ....... 3432910

[51] Int. Cl.$^4$ .................... B32B 31/04; B32B 31/18
[52] U.S. Cl. .................... 156/517; 156/256; 156/519; 156/552
[58] Field of Search ............. 156/256, 517, 519, 521, 156/552, 568, 571

[56] References Cited

U.S. PATENT DOCUMENTS 3,963,557 6/1976 Patterson ........................... 156/519
4,519,865 5/1985 Bradler et al. ..................... 156/568

Primary Examiner—Caleb Weston
Attorney, Agent, or Firm—Antonelli, Terry & Wands

[57] ABSTRACT

The present invention provides a process and apparatus for the separation of strip sections from a first moving material web, for the subsequent application of these strip sections on discrete areas lying at a distance one behind the other of a likewise moving second material web, wherein the predetermined distance is achieved by moving the separated strip sections apart. In the case of a transfer of the strip section to the second material web, the strip sections and the second material web are kept at an equal constant speed during the entire transfer process. The apparatus for carrying out the process comprises a multiplicity of conveying elements rotating on a circular periphery. In the peripheral direction, the conveying elements have a distance to one another which changes during each rotation. A bipartite lever rod system takes care of this change of distance between the conveying elements which system always connects a conveying element with a common driving disc. The lever rod system is controlled on a curve path in such a way that the conveying elements may rotate at a constant speed over extended stretches.

6 Claims, 3 Drawing Figures

APPARATUS FOR SEPARATING AND APPLYING OF SECTIONS OF STRIPS ON AREAS OF A MATERIAL WEB LYING AT A DISTANCE ONE BEHIND THE OTHER

The invention relates to a process for the separation of elastically stretched strip sections of a first moving material web and the subsequent application of these strip sections to discrete areas, lying one behind the other at a predetermined distance, of a second material web which is likewise moving, and each separated strip section being accelerated for a length of time until a predetermined distance between the separated strip section and a succeeding strip section has been reached.

U.S. Pat. No. 3,963,557 demonstrates a process for applying a section of definite length separated from an endless ribbon fed continuously at equal speed, at distances from one another, and in an adhesive manner onto a second ribbon likewise fed continuously at equal speed.

This process is achieved by the fact that strip sections separated at a definite length from the first ribbon material are received by conveying elements and are transferred to the second web, the conveying speed of which increases until the strip sections reach a predetermined distance to the succeeding strip section. After transfer of the strip section to the second material web, the conveying speed of the pertinent conveying element again returns to the lower value at which again a new strip section is taken over from the first material web for transfer to the second material web.

In the case of the apparatus for carrying out the process of U.S. Pat. No. 3,963,557, the conveying elements rotate at variable angular speed around an axle. The variable angular speed will be achieved through the fact that the conveying elements rotating on the axle are driven by a driving disc which rotates on a parallel displaced axle and which has radial guide grooves with which the drivers attached to the conveying elements engage for the transfer of power. By such an eccentric mounting of the driving disc and of the rotating conveying elements, the drivers of the conveying elements travel during a rotation of a conveying element within the guide groove of the driving disc from a radially minimal distance to the rotational axle of the driving disc up to a radially maximum larger distance. This shifting of the point of engagement varying in radial direction between the driving axle and the conveying element causes the desired variable angular speed of the conveying elements during their rotation.

Thus, the angular speed perforce varies over the entire peripheral area, that is to say that on the entire periphery there is no point at which the conveying elements do not change their speed. It is disadvantageous when sections separated from a first ribbon and, for example, provided with adhesive, are to be applied in an adhesive manner onto a second web brought up continuously at equal speed. Accordingly, since the speed of the conveying element always changes, this prevents the sections to be applied to the second web from being able to be transferred without a relative movement between the section to be applied and the second web. However, a transfer in the case of a lacking relative speed, that is to say, equal speed of the section to be applied and of the second web is frequently absolutely required in order to achieve a perfect adhesive binding of the sections with the second web and to be sure especially whenever a contact adhesive is used. At the same time, it is to be taken into consideration that in practice, the application is accomplished at extremely high speed, and therefore the contact times are perforce extremely short. In the case of an always present relative speed between the second ribbon and the conveying elements, practically only the application of relatively short sections onto the second ribbon is possible. On the other hand, in the case of longer sections to be applied, impermissible tensions would occur between the section to be applied and the second ribbon during the application process. The essential task of the invention is to avoid this disadvantage.

This task will be solved through the fact that the strip section is moved only a distance corresponding to at least the length of the strip at a constant speed and in doing so will be transferred completely to the second material web.

Another object of this invention is to provide a process wherein each strip section which is separated from the first material web is moved at a constant speed at least briefly, so that a more effective development insofar as the separation of a strip section from the first material web may take place in an area of constant speed of the section to be separated. Also, an object of this invention is to provide an apparatus for carrying out the process of the invention.

The apparatus, according to the present invention, comprises a plurality of conveying elements which rotate on an axle with a rotating receiving surface, and one conveying element lying on an equal circular circumference and capable of being put against two material webs one lying behind the other. The conveying elements have a distance in relation to one another and vary per rotation of this angular speed after a certain prearrangement in such a way that in a first fixedly prearranged position in which the first material web is put onto the receiving surfaces of the conveying elements. Furthermore, the two conveying elements lie one behind the other at a minimum distance, from which the conveying element which is the forward one in the direction of movement departs while increasing the distance, at an angular speed greater than the adjacent conveying element. After reaching a distance in which the strip sections carried along are to be applied to the second material web, the conveying elements transfer the strip sections in a second, fixedly predetermined position to the second material web.

Moreover, the apparatus, according to the present invention, includes a driving disc which rotates on an axle of a conveying element; a first lever which is rotatably mounted on a graduated circle of the driving disc of each conveying element in an axle which is parallel to the axle of the conveying elements, wherein the end of each first lever lying radially inside is guidable in a predetermined curve path; a second lever articulated at each radially outside lying end of the first lever so that the second lever is always articulately connected with a conveying element and that the points of articulation for the second lever lie at the same place on each conveying element; and the curve path is designed such that the second levers, counting from their pertinent point of articulation on the conveying element, change their angle in relation to the graduated circle on which the points of articulation lie in order to achieve variable speeds of the conveying elements driving one rotation. An effective form of the curved path for the guidance of the levers, according to the present invention, is that the curve path is divided into four sections (a, b, c, d), of which sections a and c are concentric, circular arcs with a center of curvature in the driving axis, section b is a curve path with the distance from the driving axis increasing from a to c, and section d is a curve path with the distance from the driving axis decreasing from c to a. In the case of this form, the circular arc sections a and c of the curve running concentrically around the driving axle take care that in the case of a guidance of the forward segments on these curved sections, a constant angular speed of the conveying element will be maintained. This angular speed agrees with the angular speed of the driving disc. In a section b of the curve path in which the articulating points of the levers guiding the forward segments move away during the rotation of the conveying elements from the driving axle, the angular speed of the lever element, guided by the pertinent lever, will be decreased to values which lie below the angular speed of the driving disc.

In the section d of the curved path, the articulating points of the levers guiding the conveying elements are moved during the rotation toward the driving axle with the consequence that an acceleration of the conveying elements takes place at a speed which lies above the angular speed of the driving disc.

The size of the angular areas across which the individual curve sections extend may be freely selected within large limits.

Advantageously, the curve section a in which the levers of the forward elements are guided during the takeover of the second material web and its connection with the sections separated from the first web occupies an angular area of at least 150° to 180°. In this manner, the second web fed in continuously at a constant speed may be guided over a relatively large angular area in contact with the conveying element from which the strip section separated from the first web and provided with an adhesive substance, is transferred to the area of the second material web coming into question. Prerequisite for a contact between a conveying element and the second material web taking place over a larger angular area, especially whenever this second material web consists of a nonstretchable material, is a constant angular speed of the conveying element during the entire contacting time in which the conveying speed of the second material web must agree exactly with the peripheral speed of the pertinent conveying element. Otherwise, a constant feed-in speed of the second web will not be possible.

Whenever the conveying elements guided side by side at a minimal distance are maintained during a predetermined period of time in which the separation of the sections of the first web received by the conveying elements takes place by simultaneous guiding of the conveying element which is the first in the direction of rotation on the curve section c and of the succeeding conveying element on the curve section a at an equal angular speed. This equal angular speed results from the circumstance that both curve sections a and c are circular sections running concentrically in relation to the driving axle. The angular area on which the two adjacent conveying elements are guided jointly always on a concentric section of a circular arc, is freely selectable within certain limits.

The apparatus, according to the present invention, also provides that at the beginning and at the end of the receiving surface, with regard to the periphery of a conveying element, one clamping arrangement which engages, at certain angular positions of the conveying elements, is closed or opened. The clamping arrangement is an angular lever swivelable around an axis parallel to the circular arc-shaped receiving surface of the conveying elements, the leg of which angular lever may be pressed against the receiving surface of the conveying element and the other leg of which is swivelable by conducting it across a control pin on a cam plate alternatingly in the open and closing position.

Thus, the present invention provides an apparatus having a special development of the clamping arrangement at the individual conveying elements for receiving and transferring of the first web.

An embodiment by way of example is shown in the drawings.

Figure 2:
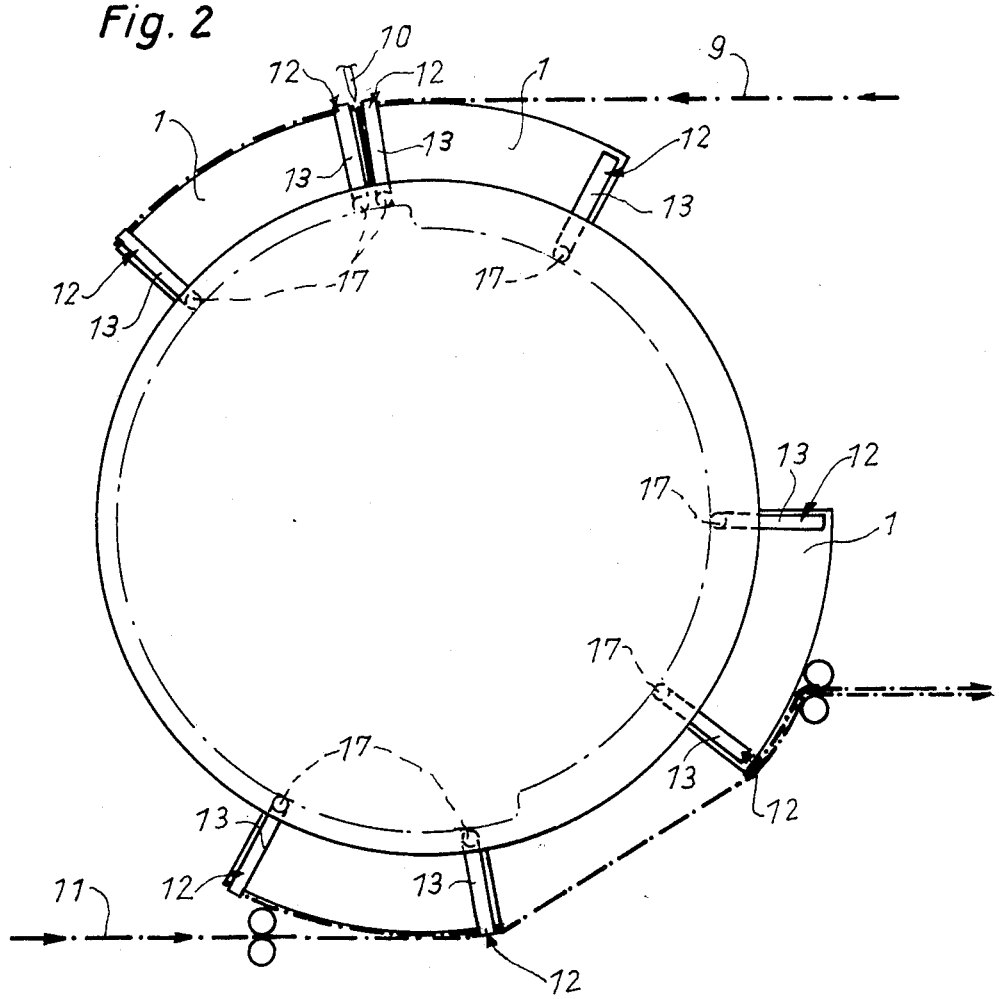
Figure 3:
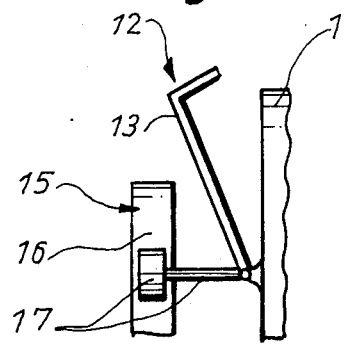

FIG. 1 shows the schematic construction of the apparatus according to the present invention, in the form of a view, FIG. 2 shows the apparatus in FIG. 1 in a schematic form in a view from behind, FIG. 3 shows a part of the clamping arrangement engaging at the conveying elements according to the view given in FIG. 1 with arrow III in the form of a cut.

The conveying elements 1 rotate with variable angular speed per rotation around the middle axis. The drive of the conveying elements 1 is accomplished by way of a driving disc 2, which rotates around the same axis as the conveying elements 1. With the driving disc 2, the individual conveying elements are always connected by way of a first lever 3 as well as a second lever 4. On the driving disc 2 itself, the first levers 3 are mounted rotatably on an identical graduated circle in axes 5 parallel to the middle axis. The second levers 4 are always mounted rotatably in the case of each conveying element 1 in the same manner as the first levers 3 at a point 6 lying at the same place as the first levers 3 in the axes 5. The first levers 3 and the second levers 4 are always connected with one another a joints 7. The ends still remaining free of the first levers are force-guided on a curve path 8. The shape of the curve path 8 is designed such that the angular speed of the conveying elements 1 changes on one rotation.

For this purpose, the cam plate 15 has sections a–d. Of these, the section a extends over an angular area of 180° and the section c over about 30°. Furthermore, these two sections are circular arcs running concentrically around the driving axle. Since the articulation points 5 and 6 of the levers 3 and 4 connected with the conveying elements are guided on circular paths concentric to the driving axle, the conveying elements 1 during guidance on the curve sections a and c always have constant angular speeds agreeing with the driving disc 2. To the contrary, in sections b and d a delay or an acceleration of the conveying elements 1 guided therein, takes place.

The first material web 9 to be separated into strip sections is fed to an area in which two conveying elements 1 are guided to one another at a minimal distance of separation. After reaching the minimal distance, a first material web 9 is fixed on the forward end in a rotational direction of the rear conveying element in rotational direction by closing of the clamping arrangement 12. Approximately simultaneously, the clamping arrangement 12 of the rear end of the forward conveying element 1, there fixates the still free end of the part of the material web 9 already located on the forward conveying element 1. Then, the two adjacent forward elements 1 move by simultaneous guidance on the curve sections a (rear conveying element) and c (forward conveying element) over an angular area of about 30° at equal speed. In this phase, a revolving knife 10 separates a first strip section lying on the forward conveying element.

The first material web 9 may be made of elastic material which is fed in in such a way that it rests on the receiving conveying element 1 in a stretched state between the clamping arrangements 12 provided there. In the case of transfer to the conveying element 1, the area of the first material web 9 lying between the clamping arrangements 12 will be coated with an adhesive by an apparatus 18.

After the separation of a strip section has been completed by the knife 10, the forward element of the adjacent conveying element 1 accelerates as a result of guidance on the curve section d. The following conveying element 1 on the contrary, slows down its speed as a result of guidance on the curve section b.

The phase of drawing apart lasts for such a length of time until the two conveying elements show a distance between their receiving surfaces for the strip section of the first material web 9 which corresponds to that which is desired on the second material web 11 onto which the strip sections are to be applied between applied strip sections.

Whenever this distance has been reached, then the guidance of the forward conveying element is taken over by the curve section a, that is to say from now on a conveying element moves over the entire length of this curve section at a constant angular speed corresponding to the driving disc 2. In this area of guidance, the second material web 11 is fed continuously to the conveying elements 1 at a speed corresponding to the peripheral speed of the conveying elements in this area and is contacted by way of a billy-roller 19 with the adhesive layer of the strip sections of the first material web 9. The second material web 11 is carried off from the peripheral path of the conveying elements 1 at about 90° after first contacting the billy-roller 19.

A quite considerable advantage of the application arrangement constructed according to the invention lies in the possibility of achieving such a long contact time between the second material web 11 and the strip sections of the first material web 9 fixated in an extended state on the conveying elements 1. At the same time, the length of the contact arrangement is freely selectable within large limits by corresponding design of the individual curve sections a-d not being in a fixed relationship to one another as well as of the fixation of the points of feeding in and carrying off for the second material web 11. The clamping arrangements 12 release the fixated, stretched strip sections on the conveying elements 1 only just prior to the deflection of the second material web 11 from the rotational path of the conveying elements.

After release of the strip sections, the conveying elements are brought up in the terminal area of the curve section a adjacent to the curve section b again for the acceptance of an additional strip section of the first material web 9 to the preceding conveying element 1 delaying its speed, and a new transfer cycle begins.

The previously mentioned clamping arrangements 12 consist of a swiveable angular lever 13, one leg of which may be pressed against the receiving surface of the pertinent conveying element 1. The swiveling takes place around the axis 14 always firmly connected with the conveying elements 1. In the case of an opened clamping arrangement 12, the short leg of the angular lever 13 is swung out completely from the area of the receiving surface of the conveying element 1. The control of the swiveling movement around the axis 14 takes place by way of a cam plate 15. In this cam plate 15, a control curve 16 has been provided with which a control pin 17 engages firmly connected with the angular levers 13.

The receiving surfaces of the conveying elements 1 for the strip sections of the first material web 9 may naturally also be provided with any other type of fixing arrangements such as, for example, suction bores. On the other hand, it will also be necessary that the control of the clamping arrangements 12 provided here does not have to take place by way of a cam plate, but it may be realized just the same hydraulically.

The process of the invention and the apparatus described for it by way of example are suitable especially when elastic ribbon is to be applied, like for example in the case of diapers, in the area of the leg section, in a stretched state limitly merely to the area in which lies the leg section of the diapers to be held up. In the case of diapers, we are preferably dealing with disposalable diapers which are obtained by separation from a material web consisting of several components. In the case of the production of such diapers, it is possible with the process of the invention and the apparatus described for it, to apply the elastic ribbon to be applied in the leg area continuously from an endless roll, and nevertheless to apply the individual strip sections at a distance in relation to one another onto the moving diaper material web while maintaining sufficiently long contact times.

What is claimed is:

1. An apparatus for separation of elastically extended strip sections from a first moving material web for the subsequent application of the strip sections to discrete areas lying at a predetermined distance one behind the other of a likewise moving second material web in the case of which each strip section just separated away from a subsequent strip section for such a length of time until the predetermined distance between them has been reached, wherein it is then moved over a distance corresponding at least to a length of the strip at a constant speed and at the same time it is completely transferred to the second material web, wherein a plurality of conveying elements rotate on an axle with a rotating receiving surface and one of said conveying elements lying on an equal circular circumference is capable of being put against two material webs one lying behind the other, the conveying elements have a predetermined distance in relation to one another and vary per rotation of their angular speed in such a way that in a first fixedly predetermined position in which the first material web is put onto the receiving surfaces of the conveying elements, so that two conveying elements lie one behind the other at a minimal distance, from which the conveying element which is the forward one in a direction of movement departs while increasing the distance, at an angular speed greater as compared to the adjacent, following conveying element, and after reaching a distance in which the strip sections carried along are to be applied to the second material web, transfer the strip sections in a second, fixedly predetermined position to the second material web, the apparatus comprising:

a driving disc which rotates on the axle of the conveying element;

a first lever which is mounted rotatable in an axle on a graduated circle of said driving disc parallel to the axle of the conveying elements;

a radially inner end of said first lever is guidable on a predetermined curved path;

a second lever articulated at a radially outer end of said first lever;

said second levers being articulately connected with said conveying element;

the points of articulation for said second levers lie at the same place on each conveying element; and said curved path being designed such that said second levers counting from their pertinent point of articulation on said conveying element change their angle in relation to the graduated circle on which these points of articulation lie in order to achieve variable speeds of said conveying elements during one rotation.

2. An apparatus according to claim 1, characterized in that during the separation of the strip sections from the first material web by a knife the adjacent conveying elements have a minimal distance of separation, and that after a predetermined period of time the conveying element, which is the forward one in the rotational direction, is guided on said third section while the adjacent succeeding conveying element is guided on said first section of curve path.

3. An apparatus according to claim 1, wherein at the beginning and at the end of the receiving surface, with regard to the periphery of a conveying element, one clamping arrangement which engages, at certain angular positions of the conveying elements, is closed or opened, so that the clamping arrangement is an angular lever swivelable around an axis parallel to a circular arc-shaped receiving surface of the conveying elements, a first leg of said angular lever may be pressed against the receiving surface of the conveying element and a second leg of of said angular lever is swivelable by conducting it across a control pin on a cam plate alternatingly in the open and closing position.

4. An apparatus according to claim 1, wherein said curved path is divided into four sections, of which the first and third sections are concentric, circular arcs with a center of curvature in the driving axis, the second section is a curve path with the distance from the driving axis increasing from said first section to said third section, and the fourth section is a curve path with the distance from the driving axis decreasing from said third section to said first section.

5. An apparatus according to claim 4, wherein the angular areas over which said four sections of the said curved path extend, are freely selectable.

6. An apparatus according to claim 4, wherein said first section serves for the guidance of the conveying elements during the takeover of the second material web and its connection with the strip sections of the first material web, and which extends over an angular area of at least 150° to about 180°.

* * * * *